ize. The invention also concerns a clear, colorless, hydrogel
United States Patent [19]

Tseng et al.

[11] Patent Number: 5,716,634
[45] Date of Patent: *Feb. 10, 1998

[54] CLEAR, HOMOGENIZED, FLOWABLE HYDROGEL OF CROSSLINKED N-VINYL LACTAM POLYMER

[75] Inventors: Susan Y. Tseng, Staten Island, N.Y.; Jui-Chang Chuang, Wayne; Philip F. Wolf, Bridgewater, both of N.J.

[73] Assignee: ISP Investments Inc., Wilmington, Del.

[*] Notice: The term of this patent shall not extend beyond the expiration date of Pat. No. 5,614,583.

[21] Appl. No.: 743,697

[22] Filed: Nov. 6, 1996

Related U.S. Application Data

[63] Continuation-in-part of Ser. No. 528,383, Sep. 13, 1995, Pat. No. 5,614,583.

[51] Int. Cl.⁶ .............................. A61K 9/70; A61K 7/135
[52] U.S. Cl. ..................... 424/445; 424/62; 424/63; 424/443
[58] Field of Search ............................ 524/548; 526/264; 424/78.25, 78.24, 445

[56] References Cited

U.S. PATENT DOCUMENTS

| 3,166,525 | 1/1965 | Perry | 524/548 |
| 5,426,163 | 6/1995 | Buehler et al. | 526/264 |

FOREIGN PATENT DOCUMENTS

| 9207011 | 4/1992 | WIPO | 526/264 |

*Primary Examiner*—Peter F. Kulkosky
*Attorney, Agent, or Firm*—Marilyn J. Maue; Walter Katz; Joshua J. Ward

[57] ABSTRACT

This invention relates to a crosslinked N-vinyl lactam polymer in the form of a stable, clear, flowable homogenized hydrogel composed of microparticles which can be passed through a screen of between about 40 and about 350 mesh size. The invention also concerns a clear, colorless, hydrogel which is required as a carrier for a cosmetically or pharmaceutically active substance such as a hair or skin conditioner and cosmetic or pharmaceutical skin base.

14 Claims, No Drawings

CLEAR, HOMOGENIZED, FLOWABLE HYDROGEL OF CROSSLINKED N-VINYL LACTAM POLYMER

This application is a continuation-in-part of Ser. No. 08/528,383, filed Sep. 13, 1995, now U.S. Pat. No. 5,614,583.

BACKGROUND OF THE INVENTION

Crosslinked vinylpyrrolidone polymeric powder has been prepared by rapid proliferous polymerization at high temperatures as described, for example, in U.S. Pat. No. 5,391,668. U.S. Pat. Nos. 5,089,910; 5,130,388 and 5,015,708 also describe processes for crosslinking vinyl lactam polymers to produce a powdery product. More recently, processes for free radical initiated polymerization and crosslinking of N-vinyl lactam monomers and comonomers have been developed which produce substantially solid formed or molded hydrogel products. These processes are described in U.S. Pat. Nos. 5,280,049; 5,362,796 and 5,354,823; however the products produced therein do not provide flowable hydrogels composed of micronized particles.

Accordingly, it is an object of the present invention to produce a crosslinked N-vinyl lactam polymer in a unique form such as a clear flowable micronized hydrogel suitable as a carrier for cosmetically and/or pharmaceutically active compounds in a cream, lotion or ointment formulation or as a moisturizer applied directly to the skin or hair.

Another object is to provide a clear, liquid film which facilitates release of wound dressings and which extends the efficacy of the medicament over longer periods of treatment without causing discoloration of the skin or hair.

Still another object is to provide a homogenized cosmetic base film which is invisible on the hair or body and which accepts other cosmetic or pharmaceutical applications.

These and other objects of this invention will become apparent from the following description and disclosure.

THE INVENTION

The clear, flowable micronized hydrogel product of this invention can be prepared by (1) forming a uniform liquid mixture of
  (a) between about 10 and about 30 wt. % of a polymerizable reactant containing at least 55% N-vinyl lactam monomer;
  (b) between about 0.01 and about 5 wt. % crosslinking agent;
  (c) between about 60 and about 90 wt. % solvent and
  (d) between about 0.1 and about 5 wt. % of a free radical initiator having a 10 hour half life temperature below the boiling point of said solvent;

(2) in the absence of agitation and in an inert atmosphere, heating the mixture to between about 50° and about 80° C. for a period of from about 1 to about 5 hours to begin polymerization without displacement of the solvent medium, and then raising the temperature to between about 100° and about 145° C. for an additional period of from about 0.5 to about 3 hours or until completion of the reaction;

(3) recovering the crosslinked polymer in the form of a rubbery intermediate and digesting said intermediate in water to extract and remove soluble monomer, linear polymer and other residuals in the aqueous phase;

(4) recovering a clear, formed, crosslinked N-vinyl lactam polymer as a hydrogel mass of from about 0.5 to about 15 wt. % solids, preferably from about 1 to about 10 wt. % solids, and (5) subjecting said hydrogel mass to high speed, high shear agitation with a mixing device having a mechanical stirrer operating at between about 5,000 and about 50,000 rpm, preferably at between about 7,000 and about 35,000 rpm, to homogenize the hydrogel mass and to form flowable hydrogel microparticles which can be pushed through a sieve having openings of between about 40 and about 350 mesh. The stirrer or propeller speed is important since, below 5000 rpm, microparticles are not formed within a reasonable time frame; whereas above 50,000 rpm excess heat is generated sufficient to evaporate solvent below 80% of the hydrogel and thus destroy its flowable property. Vigorous mixing is generally effected over a period of from about 15 minutes to about 1 hour, although longer mixing times can be employed without adverse effect. Particularly good agitation is achieved with a cascade mixer or with a mixer having a housed impeller which breaks up a hydrogel mass introduced through an inlet port and directs hydrogel particles through an outlet port.

The unique product of this invention is preferably prepared by the above method which is described in more detail in copending allowed U.S. patent application, Ser. No. 528,383 and which is incorporated herein by reference.

The present product consists essentially of a clear, flowable, 0.5 to 6% crosslinked N-vinyl lactam polymer in the form of hydrogel microparticles. Most desirably, the clear, flowable hydrogel microparticles of the present invention recovered from the high speed mixer pass through a 70–150 mesh screen and the micronized gel has a Brookfield viscosity* of from about 10,000 to about 70,000 cps; although hydrogel viscosities as low as 7,000 cps up to about 90,000 are also considered within the scope of this invention.

*RV Model, #7 spindle, 20 rpm, 25° C.

The clarity and flowability of the present product makes it ideal for application as a thin film for protecting the skin or hair against pollution and additionally as a retentive base over which other cosmetic components can be applied. The superior conditioning properties of instant flowable, homogenized hydrogel product is attributable in part to its ability to absorb atmospheric moisture and to minimize evaporation of moisture from the skin or hair during treatment. Hence, as a carrier for skin rejuvenants or hair bleaches and dyes, the epidermis or hair follicles are not damaged by irritation, dryness or brittleness. The microparticle size of the hydrogel is largely responsible for its flowability to obtain easy and uniform application and provides for intimate admixing with active cosmetic or pharmaceutical agents in formulations applied as stable creams, lotions, ointments and the like. For example, the stable, homogenized microhydrogels of the present invention, can be combined with antiseptic agents, e.g. PVP/I or PVP/peroxide, to provide a thin, invisible film having sustained and gradual release of the disinfectant. The flowable property of the present product allows for superior penetration of a wound or wound dressing which extends use of the dressing and provides gradual release of the medicament over an extended period. Additionally, the film forming properties of the present water insoluble hydrogel permits formulation with water soluble complexes, e.g. PVP/I and PVP/$H_2O_2$ and other water soluble components, to form a water resistant coating. As indicated above, the unformulated hydrogel product herein described can be employed directly to any porous surface, e.g. skin, hair, leather, wood etc., as a moisturizer without discoloration of the substrate or it can be used in formulation with other active components suitable for the treatment of such substrates. These and other valuable properties will become known by reason of the following disclosure.

For the purpose of reducing shippment costs, the homogenized hydrogel herein described can be subjected to drying so as to provide a concentrated, finely divided particulate solid which is readily redispersible in water to its original clear homogenized form. For example, the product can be subjected to freeze drying for a period of from about 2 to about 24 hours at a temperature of between about −85° C. and −40° C., preferably between −80° C. and about −60° C. for a period of from 5 to 10 hours. Alternative drying procedures including drum drying, belt drying and spray drying at 120° C. to about 140° C. are also contemplated for reducing volume for shippment.

The clear, micronized, homogenized hydrogel of this invention is derived from the homo- or co-polymerization of N-vinyl pyrrolidone and/or N-vinyl caprolactam which is between about 0.01 and about 5% crosslinked, preferably between about 0.1 and about 2% crosslinked, with a suitable polyfunctional crosslinking agent.

As indicated, the N-vinyl lactam monomer or oligomer may be combined with a polymerizable non-lactam comonomer, preferably in an amount not more than 30% comonomer. Suitable comonomers are those which are soluble in the reaction mixture and include olefinically unsaturated compounds such as another N-vinyl formamide, vinyl acetate, ammonium and alkali salts of acrylic acid and methacrylic acid, acrylamide, methacrylamide, lower alkyl acrylates or methacrylates, acrylonitrile, vinyl chloride, hydroxyalkyl acrylates or methacrylates, hydroxybutyl vinyl ether, quaternized dimethylamino lower alkyl acrylates or methacrylates and the like.

Representative of the crosslinking agents which can be employed are diallylimidazolidone; divinyl ether of diethylene glycol; pentaerythritol triallyl ether (PETE); triallyl-1,3,5-triazine-2,4,6-(1H,3H,5H) trione (TATT); ethylene glycol diacrylate; 2,4,6-triallyloxy-1,3,5-triazine; N-vinyl-3(E)-ethylidene pyrrolidone (EVP); 1,7-octadiene; 1,9-decadiene; divinyl benzene; methylenebis(methacrylamide); methylenebis(acrylamide); N,N-divinylimidazolidone; ethylene glycol diacrylate; ethylidene bis(N-vinyl pyrrolidone) (EBVP); etc.

The crosslinked polymer is saturated in from about 5 to about 800 volumes of water and digested for a period of from about 5 hours to about 2 days. The resulting swelled hydrogel is then homogenized in a high speed mixer at the above disclosed rpm to provide the clear, flowable hydrogel of uniformly dispersed microparticles which contains polymer which is between about 0.01 and about 5% crosslinked; i.e. 0.5–15 wt. % polymer, between about 70 to 99.5 wt. % water and between about 0 to about 20 wt. % of an innocuous additive or a material which is chemically inactive to the hydrogel, e.g. colorant, medicinal or other ingredients suitable for particular needs which may be added upon option.

Preferred polymers in the flowable homogenized hydrogel of this invention are those derived from N-vinyl pyrrolidone homopolymer or N-vinyl pyrrolidone/N-vinyl caprolactam copolymer which are crosslinked with EVP, EBVP or divinylimidazolidone. Most preferred is the EVP crosslinked N-vinyl pyrrolidone homopolymer.

The present flowable hydrogel possesses many beneficial properties. For example, the present product maintains its original viscosity over a broad pH range, thus enabling formulation to a desired consistency with both acid and basic components. The active components can be those used in personal care and pharmaceutical applications as well as in creams and lotions for leather and wood treatment. More specifically, the present products are valuable carriers in concentrations of from about 75 to about 99.9 wt. %, preferably from about 80 to about 93 wt. %, of the total composition containing an active component. Suitable active components include those employed in sun blocks; hair bleaches; depilation; skin depigmentation, rejuvenation, disinfection, moisturizing, softening and defoliantation. Since the present carriers are colorless and not irritating to the skin, they can be applied in formulations over a wound or employed in wound dressings without staining of clothing and without the customary stinging or burning sensation on the skin. The flowable hydrogels of this invention are more skin substantive than their non-flowable counterparts and prolong the efficacy of active components by forming a skin barrier which resists evaporation. As a dentifrice fixing agent, the flowable property of instant hydrogels permits better conformity with gums thus providing a more comfortable fit. These and many other uses of the present products will be suggested by the unique properties of the flowable hydrogels described herein.

Having generally described the invention, reference is now had to the following examples which illustrate preferred embodiments concerning the preparation and use of the present products, which examples are not to be construed as limiting to the scope of the invention as more broadly defined above and in the appended claims.

EXAMPLE 1

A homogeneous solution of 10.84 grams of N-vinyl pyrrolidone (VP), 0.0479 gram N-vinyl-3(E)-ethylidene pyrrolidone (EVP), 42.24 grams of distilled water and 0.1192 gram of tert-butyl peroxypivalate (LUPERSOL 11) was reacted under 25 mm Hg of nitrogen at 60° C. for 1.5 hours and then at 120° C. to 140° C. for 1.5 hours, after which the solution was allowed to cool to room temperature and the resulting rubbery product was then recovered and was introduced into about 800 volumes of distilled water and digested for 15 hours with simultaneous removal and replacement of the water until the mother liquor is free of residual monomer and soluble poly-(N-vinylpyrrolidone). During the above water digestion step, the rubbery product swelled to a clear, transparent hydrogel mass having a gel volume of 18 grams water per gram of crosslinked polymer. This hydrogel product, was then introduced into a Ross homogenizer where, at 7,000 rpm the hydrogel mass is reduced to flowable hydrogel having a Brookfield viscosity of 30,000 cps which hydrogel is composed of colorless, clear particles which pass through a 40 mesh screen.

EXAMPLE 2

Hydrogel products obtained from crosslinking the compositions shown in Table 1 for 1 hour at 70° C. followed by 2 hours at 100° C. and digested in 10 fold volumes of water over a period of 16 hours to remove contaminants, were recovered as a hydrogel mass having the indicated wt. % solids. These samples were separately homogenized in a Ross Homogenizer at room temperature operated 7,000 rpm for 30 minutes, after which the products were recovered and particle size determined. All products except product A passed through a 70 mesh screen. Sample A passed through a 40 mesh screen. The % solids in the homogenized microgel was as follows:

| | | |
|---|---|---|
| A = 5.4 | D = 2.8 | G = 6.1 |
| B = 3 | E = 3 | |
| C = 5 | F = 1.84 | |

All of these products, regardless of % solids content were clear, flowable hydrogels.

TABLE 1

| | WEIGHT (GRAMS) | | | | | | |
|---|---|---|---|---|---|---|---|
| Sample | A | B | C | D | E | F | G |
| VP | 39.84 | 39.93 | 49.8 | 39.92 | 11.95 | 9.543 | 319.04 |
| EVP | 0.16 | 0.08 | 0.2 | 0.08 | 0.05 | 0.0454 | 0.96 |
| Lupersol | | | | | | | |
| 554* | 0.398 | 0.4 | 0.73 | 0.336 | 0.12 | — | 3.35 |
| 11** | — | — | — | — | — | 0.51 | |
| $H_2O$ | 160 | 160 | 200 | 160 | 48 | 90 | 1280 |
| % Solids in digested Hydrogel | 5.9 | 3 | 5 | 2.8 | 3 | 1.84 | 6.11 |

*tert-amyl peroxypivalate
**tert-butyl peroxypivalate

The products of the foregoing examples can be admixed at room temperature for 30 minutes with 0.05 wt. % of PVP/I disinfectant to provide a water insoluble creamy composition which can be applied as a thin film to a gauze pad for use as a wound dressing. Also, these hydrogel products can be mixed with an effective amount of a sun blocking agent or applied directly to the skin in a thin layer as a water insoluble moisturizer. Further, the present hydrogels can be employed as a stable carrier for standard concentrations of hair bleach, hair dye and hair straightening agents to minimize skin irritation and hair dryness or brittleness while imparting a silky, soft feel. Still further, the above products can be applied to leather for preservation and softening effects which qualities are enhanced by the hydrogel microparticle penetrating properties. Alternatively, about 0.5–5 wt. % of the present product can be added to a commercial liquid leather treating formulation, e.g. ARMOROL, to provide a nourishing cream which resists drying by exposure to sunlight.

Pharmaceutical applications for the homogenized hydrogel microparticles of the invention are also useful as a water barrier over cuts and burns or as a moisturizing carrier for antifungal or antiseptic creams and lotions such as those containing zinc oxide, hydrocortisone, sodium perborate, iodine, hydrogen iodide, oil of wintergreen, and the like.

When used in a formulation, the present hydrogel can replace all or a portion of the carrier normally employed in a cosmetic or pharmaceutical formulation. However, when used as the sole carrier, the composition generally contains between about 0.01 and about 15 wt.% of the active ingredient. These and other beneficial uses of the present flowable hydrogel products will become apparent and are within the scope of this invention.

The following examples describe the preparation of several cosmetic and pharmaceutical compositions.

EXAMPLE 3

The hydrogel of sample 1A was freeze-dried at −80° C. to form a powder. Into an 8 ounce jar, containing 2.5 g of the resulting crosslinked PVP powder was introduced, under gentle mixing conditions and at room temperature, 83.5 g of pH 4 buffer solution and 2.0 g of hydrogen peroxide (30%). After mixing for 5 minutes, the jar contents were refrigerated overnight after which the gel containing 0.69 wt. % $H_2O_2$ was formed and recovered as the product. Observation after 6 weeks showed the product to be stable. The distinfectant product of this example can be spread on the face as a treatment for ache.

EXAMPLE 4

An 8 ounce jar, containing 54.75 g of the flowable crosslinked PVP hydrogel of Sample 1A, was evaporated to a concentration of 36.5 g of hydrogel (8.1% solids) and 18.3 g of $H_2O_2$ (30% in distilled water) was then introduced with gentle mixing at ambient temperature for 10 minutes. During mixing the pH of the mixture was adjusted to 4 with about 2 drops of lactic acid. The jar contents was refrigerated overnight and the resulting product contained 10% $H_2O_2$. This product can be applied to the hair as a bleach without scalp irritation.

EXAMPLE 5

Example 4 was repeated except that 0.30 g of lactic acid (88% aqueous solution) was substituted for 18.3 g $H_2O_2$. The pH of the refrigerated product, containing 0.5 wt. % lactic acid, was 3. The product was stable when inspected after 6 weeks storage. This product is spread on the skin as a cream to effect decolorization of brownish spots.

EXAMPLE 6

Example 5 was repeated except that 81.25 g of the homogenized, flowable gel and 4.92 g of lactic acid were substituted. The refrigerated product contained 5 wt. % lactic acid and had a pH of 2. The product was found to be stable when ispected after 6 weeks. This product is useful as a skin bleach.

EXAMPLE 7

A 6.11% solids crosslinked PVP, flowable, homogenized hydrogel (80 g) containing 0.08 g of formic acid was sealed in a reactor and held at 50° C. Iodine crystals contained in a separate zone of the reactor, were vaporized and allowed to condense into the hydrogel/formic acid liquid mixture. When all of the crystals had been vaporized, the temperature of the reactor was raised to 85° C. and reaction continued for 2 hours after which no additional iodine vapor was given off and a flowable hydrogel PVP/I complex, containing 0.73% available iodine and an iodine/iodide ratio of 2:1, was formed and collected. This product can be spread over a wound to disinfect the injury without stinging. Alternatively, the product can be coated on a wound dressing and dried thereon for subsequent use.

EXAMPLE 8

A sealed, nitrogen degassed, 2 liter Büchi reactor, containing a homogeneous mixture of 319 g. vinyl pyrrolidone, 0.64 g. ethylidene vinyl pyrrolidone (EVP), 1280 g. distilled water and 1.70 g. LUPERSOL 554 was heated in a quiescent zone for 2 hours at 70° C. and then heated for an additional 2 hours at 110° C. without stirring. The reactor and contents was allowed to cool to room temperature and the resulting rubbery mass was then digested in 5 gallons of distilled water for 16 hours which involved the simultaneous removal and replacement of water until the mother liquor was free of residual monomer and soluble polymer. A swelled, clear hydrogel mass of 0.2% crosslinked polymer was recovered and then introduced into a Ross homogenizer which was operated at 7000 rpm to obtain a flowable product of particle size passable through a 60 mesh screen. The product was clear and had a Brookfield viscosity of 60,000 cps at 5.94% solids content, measured at 25° C. using Model RV and Spindle No. 7 at 20 rpm. This product was diluted to 4.33% solids without loosing clarity and was found to have a Brookfield viscosity of 38,600 cps. These products were compared with the non-homogenized crosslinked product of U.S. Pat. No. 5,242,985, Example 6, which was crosslinked to approximately the same degree (0.25%) as in the present example. Patentees' product, made up to a 5% solids concentration, as noted at column 8, lines 28–32 of the patent, was opaque white and achieved a Brookfield viscosity of only 18,000 cps. One would expect that our product at 4.33% solids would have a much lower viscosity than that found for patentees' product since the viscosity usually increases with the % solids in the gel. Also the clarity of the present products is unexpected, particularly at the higher solids content.

EXAMPLE 9

CLARITY COMPARISON

Into an 8 dram glass vial was introduced a 3% solution of the present homgenized hydrogel of Example 1. A 3% solution of the hydrogel product of Example 5 of U.S. Pat. No. 5,242,985 was placed in a similar glass vial. The vials were then placed in a HACH Turbidimeter where the turbidity value is determined by rationing the 90° scattered light against the sum of transmitted and foward scattered signals. The haze value is reported in nephelometric turbidity units (NTU) which vary directly with the degree of turbidity or haze. The following Table 2 reports the results of this comparison.

TABLE 2

|  | Sample Product of present Ex. 1 | Sample Product of Ex. 6 of U.S. 5,242,985 |
| --- | --- | --- |
| HAZE (NTU) | 26 | 1627 |
| APPEARANCE | clear | opaque white |

EXAMPLE 10

The clear, flowable hydrogel prepared in Example 8 was freeze dried at −80° C. and one gram of the resulting powder was contacted with 40 grams of aqueous ammonium hydroxide (28–30% NH$_4$OH) to provide a liquid which thickened somewhat upon mixing. The pH of this hydrogel was about 12.5, however, the properties of clarity and flowability were retained.

EXAMPLE 11

The clear, flowable hydrogel prepared in Example 8 was again freeze dried at −80° C. and one gram of the resulting powder was mixed with 45 grams of hydrochloric acid (36–38% HCl). The resulting liquid hydrogel product had a pH of about 0.5, however the clarity and flowability properties of the hydrogel were retained.

Examples 10 and 11 illustrate the stability of the hydrogel, even after drying to a powder and show that the original properties of clarity and microgel flowability are restored upon dilution over a wide pH range.

What is claimed is:

1. A clear, flowable, homogenized hydrogel of a 0.01 to 6% crosslinked N-vinyl lactam polymer formed by polymerizing monomer with from 0 to 45% of olefinically unsaturated comonomer, said hydrogel consisting of microparticles which can be passed through a screen of between about 40 to about 350 mesh size and which has a Brookfield viscosity of from about 7,000 to about 90,000 cps.

2. The clear hydrogel of claim 1 having a Brookfield viscosity of between about 10,000 and about 70,000 cps.

3. The clear hydrogel of claim 1 containing microparticles which can be passed through a screen having openings of from 60 to about 350 mesh.

4. The clear hydrogel of claim 3 wherein said microparticles can be passed through a 70–150 mesh screen.

5. The clear hydrogel of claim 1 which is a clear, colorless liquid containing between about 1 and about 6% solids.

6. A composition comprising the hydrogel of claim 1 containing between about 0.01 and about 15 wt. % of an efficacious amount of a cosmetically or bacterially active agent.

7. A wound dressing containing a dressing penetrating amount of the hydrogel of claim 1.

8. A moisturizing film of the hydrogel of claim 1 on a porous organic substrate.

9. The film of claim 8 which is a flowable paste having a Brookfield viscosity of from 50,000 to 70,000 cps.

10. The film of claim 8 which is a liquid having a Brookfield viscosity of from 7,000 to 25,000 cps.

11. A composition comprising between about 75 wt. % and about 99.9 wt. % of the hydrogel of claim 1 and between about 0.1 wt. % and about 25 wt. % of an efficacious amount of an active agent selected from the group consisting of a sun block; hair bleach; depilatant; disinfectant; breath freshener; and a skin depigmentizer, rejuvenizer, moisturizer, softening agent and exfoliating agent.

12. The composition of claim 11 wherein the active agent is a bleach containing H$_2$O$_2$.

13. The composition of claim 11 wherein the active agent is a disinfectant.

14. The composition of claim 11 containing between about 75 wt. % and 99.9 wt. % of the hydrogel of claim 1 in a strongly acidic or strongly basic solution.

* * * * *